United States Patent
Rovatti

(10) Patent No.: US 10,213,539 B2
(45) Date of Patent: Feb. 26, 2019

(54) EXTRACORPOREAL BLOOD CIRCUIT WITH NON-INVASIVE PRESSURE SENSOR

(71) Applicant: GAMBRO LUNDIA AB, Lund (SE)

(72) Inventor: Paolo Rovatti, Finale Emilia (IT)

(73) Assignee: Gambro Lundia AB, Lund (ES)

( * ) Notice: Subject to any disclaimer, the term of this patent is extended or adjusted under 35 U.S.C. 154(b) by 0 days.

(21) Appl. No.: 14/647,903

(22) PCT Filed: Oct. 29, 2013

(86) PCT No.: PCT/IB2013/059745
§ 371 (c)(1),
(2) Date: May 28, 2015

(87) PCT Pub. No.: WO2014/083448
PCT Pub. Date: Jun. 5, 2014

(65) Prior Publication Data
US 2015/0306295 A1    Oct. 29, 2015

Related U.S. Application Data

(60) Provisional application No. 61/731,036, filed on Nov. 29, 2012.

(30) Foreign Application Priority Data

Nov. 29, 2012 (EP) .................................. 12194715

(51) Int. Cl.
*A61M 1/16* (2006.01)
*A61M 1/36* (2006.01)
*A61M 1/34* (2006.01)

(52) U.S. Cl.
CPC ............ *A61M 1/1603* (2014.02); *A61M 1/16* (2013.01); *A61M 1/1601* (2014.02); *A61M 1/1621* (2014.02); *A61M 1/3403* (2014.02); *A61M 1/3639* (2013.01); *A61M 2205/18* (2013.01); *A61M 2205/3334* (2013.01); *A61M 2205/3355* (2013.01); *A61M 2205/75* (2013.01)

(58) Field of Classification Search
CPC .................................................. A61M 1/1603
See application file for complete search history.

(56) References Cited

U.S. PATENT DOCUMENTS

| | | | |
|---|---|---|---|
| 5,762,782 A | 6/1998 | Kenley | |
| 6,090,048 A | 7/2000 | Hertz | |
| 6,638,478 B1 | 10/2003 | Treu | |
| 2006/0100564 A1 | 5/2006 | Sano | |
| 2006/0270971 A1* | 11/2006 | Gelfand | A61B 5/201 604/66 |
| 2007/0000333 A1 | 1/2007 | Brugger | |
| 2012/0029408 A1 | 2/2012 | Beaudin | |
| 2012/0079886 A1* | 4/2012 | Beck | A61M 5/16854 73/756 |

FOREIGN PATENT DOCUMENTS

| | | |
|---|---|---|
| EP | 0501234 | 9/1992 |
| GB | 2417052 | 2/2006 |

* cited by examiner

*Primary Examiner* — Peter Keyworth
(74) *Attorney, Agent, or Firm* — K&L Gates LLP

(57) ABSTRACT

Extracorporeal blood treatment apparatus (1) and methods as described herein involve control of blood line pressure utilizing a non-invasive pressure sensor (16).

21 Claims, 4 Drawing Sheets

EXTRACORPOREAL BLOOD CIRCUIT WITH NON-INVASIVE PRESSURE SENSOR

This application is a U.S. National Stage Application of International Application No. PCT/IB2013/059745, filed Oct. 29, 2013, which was published in English on Jun. 5, 2014 as International Patent Publication WO 2014/083448 A1, which claims the benefit under 35 U.S.C. 119(e) of U.S. Provisional Application No. 61/731,036 filed Nov. 29, 2012. International Application No. PCT/IB2013/059745 also claims priority to European Application No. 12194715.4, filed Nov. 29, 2012.

Apparatus for controlling pressure of a blood line in an extracorporeal blood treatment apparatus and associated methods are described herein.

BACKGROUND

Extracorporeal blood treatment involves taking the blood from a patient, treating the blood outside the patient, and returning the treated blood to the patient. Extracorporeal blood treatment (hemodialysis, hemofiltration for example) is typically used to extract undesirable matter or molecules (apheresis, plasmapheresis for example) from the patient's blood, and/or to add beneficial matter or molecules to the blood. The treatment is typically performed by sampling the patient's blood in a continuous or intermittent flow, by introducing the blood into a primary chamber of a filter that is defined, at least in part, by a semi-permeable membrane. The semi permeable membrane may selectively allow the unwanted matter contained in the blood pass through the membrane, from the primary chamber to the secondary chamber, and may selectively allow the beneficial matter contained in the liquid going into the secondary chamber pass through the membrane to the blood going into the primary chamber, according to the type of treatment.

Extracorporeal blood treatment is used with patients incapable of effectively eliminating matter from their blood. One example is a patient who is suffering from temporary or permanent kidney and/or liver failure. These and other patients may undergo extracorporeal blood treatment to add to or to eliminate matter from their blood, to maintain an acid-base balance, to eliminate excess body fluids, etc.

In the case of the aforementioned treatments of blood and methods of removing a blood component, the source of fluid is formed by the vascular circuit of the patient/donor, and the fluid is the blood of the patient/donor, which blood, pumped from an artery, is caused to circulate in a blood treatment apparatus (hemodialyzer, hemofilter, plasma filter, centrifuge, etc.) and, once freed of its impurities or having a fraction of one of its components reduced, is re-injected into a vein of the patient/donor.

Due to the geometry of a hemodialysis filter and the presence of microbubbles inside the semi-permeable membrane of the hemodialysis filter or due to the initiation of a blood clotting phenomena or other circumstance, the extracorporeal circuit and particularly the inlet of the hemodialysis filter can experience high pressure. These high pressures or high pressure transients can cause mechanical hemolysis in the red blood cells of the blood and/or malfunction or damage to the extracorporeal blood line. Thus it is desired to provide for early detection of high pressure in the extracorporeal circuit to prevent mechanical hemolysis in the red blood cells of the blood or other malfunction or damage.

SUMMARY

This disclosure relates to extracorporeal blood treatment apparatus and methods described herein involve non-invasive pressure sensing of a blood circuit.

In one aspect, one or more embodiments of the apparatus configured to remove one or more substances from blood as described herein may include: a primary filter comprising a first semipermeable membrane separating a blood compartment from a dialysate loading compartment; a blood circuit configured to move blood through the blood compartment of the primary filter using a blood pump. The blood circuit comprises a blood line configured to move blood from the blood pump to the blood compartment of the primary filter. A non-invasive pressure sensor is disposed about an exterior surface of the blood line. The non-invasive pressure sensor pressure is configured to sense pressure in the blood line. A control unit is operably connected to the non-invasive pressure sensor and control elements of the blood circuit. The control unit is configured to monitor a blood circuit pressure value using the non-invasive pressure sensor and operate the control elements of the blood circuit based on the monitored blood circuit pressure value.

In one or more embodiments of the apparatus configured to remove one or more substances from blood as described herein, the non-invasive pressure sensor is in direct contact with the exterior surface of the blood line.

In one or more embodiments of the apparatus configured to remove one or more substances from blood as described herein, the blood line comprises polymeric tubing, and the non-invasive pressure sensor is in direct contact with an exterior surface of the polymeric tubing.

In one or more embodiments of the apparatus configured to remove one or more substances from blood as described herein, the non-invasive pressure sensor is in direct contact with opposing sides of the polymeric tubing.

In one or more embodiments of the apparatus configured to remove one or more substances from blood as described herein, the non-invasive pressure sensor is configured to sense a force applied by the blood to the polymeric tubing.

In one or more embodiments of the apparatus configured to remove one or more substances from blood as described herein, the non-invasive pressure sensor is fixed to a housing of the apparatus and the blood line is removable from the non-invasive pressure sensor.

In one or more embodiments of the apparatus configured to remove one or more substances from blood as described herein, the control unit is configured to take action once the blood circuit pressure value is not within a predetermined value range.

In one or more embodiments of the apparatus configured to remove one or more substances from blood as described herein, control unit action includes providing an alarm indication.

In one or more embodiments of the apparatus configured to remove one or more substances from blood as described herein, the control unit action includes altering a flow rate of the blood pump.

In one or more embodiments of the apparatus configured to remove one or more substances from blood as described herein, the non-invasive pressure sensor has an accuracy that is not less than ±25 mmHg.

In a second aspect, one or more embodiments of a method of moving blood through a blood circuit in an extracorporeal blood treatment apparatus that includes a primary filter comprising a first semipermeable membrane separating a blood compartment from a dialysate loading compartment;

a blood circuit configured to move blood through the blood compartment of the primary filter using a blood pump. The blood circuit comprises a blood line configured to move blood from the blood pump to the blood compartment of the primary filter. A non-invasive pressure sensor is disposed about an exterior surface of the blood line. The non-invasive pressure sensor pressure is configured to sense pressure in the blood line. A control unit is operably connected to the non-invasive pressure sensor and control elements of the blood circuit. The control unit is configured to monitor a blood circuit pressure value using the non-invasive pressure sensor and operate the control elements of the blood circuit based on the monitored blood circuit pressure value. The one or more embodiments of the method as described herein may include: pumping blood through the blood circuit at a blood flow rate with the blood pump; measuring blood circuit pressure with the non-invasive pressure sensor; and altering control elements of the blood circuit based on the measured blood circuit pressure.

In one or more embodiments of the method of moving blood through a blood circuit in an extracorporeal blood treatment apparatus as described herein, the altering step comprises altering a flow rate of the blood pump when the measured blood circuit pressure is greater than a predetermined value.

In one or more embodiments of the method of moving blood through a blood circuit in an extracorporeal blood treatment apparatus as described herein, the altering step comprises providing an alarm indication or deactivating the blood pump when the measured blood circuit pressure indicates that the blood circuit is not engaged within the non-invasive pressure sensor or when the measured blood circuit pressure is greater than a predetermined value.

In one or more embodiments of the method of moving blood through a blood circuit in an extracorporeal blood treatment apparatus as described herein, further comprising removing the blood line from the non-invasive pressure sensor upon completion of a treatment.

In a third aspect, one or more embodiments of a use of the extracorporeal blood treatment apparatus described herein to prevent blood line pressure from exceeding a predetermined value, is described.

The above summary is not intended to describe each embodiment or every implementation of the extracorporeal blood treatment apparatus and methods described herein. Rather, a more complete understanding of the disclosure will before apparent and appreciated by reference to the following Description of Illustrative Embodiments and claims in view of the accompanying figures of the drawings.

BRIEF DESCRIPTION OF THE VIEWS OF THE DRAWING

The disclosure may be more completely understood in consideration of the following detailed description of various embodiments of the disclosure in connection with the accompanying drawings, in which.

DESCRIPTION OF ILLUSTRATIVE EMBODIMENTS

Figure 1:
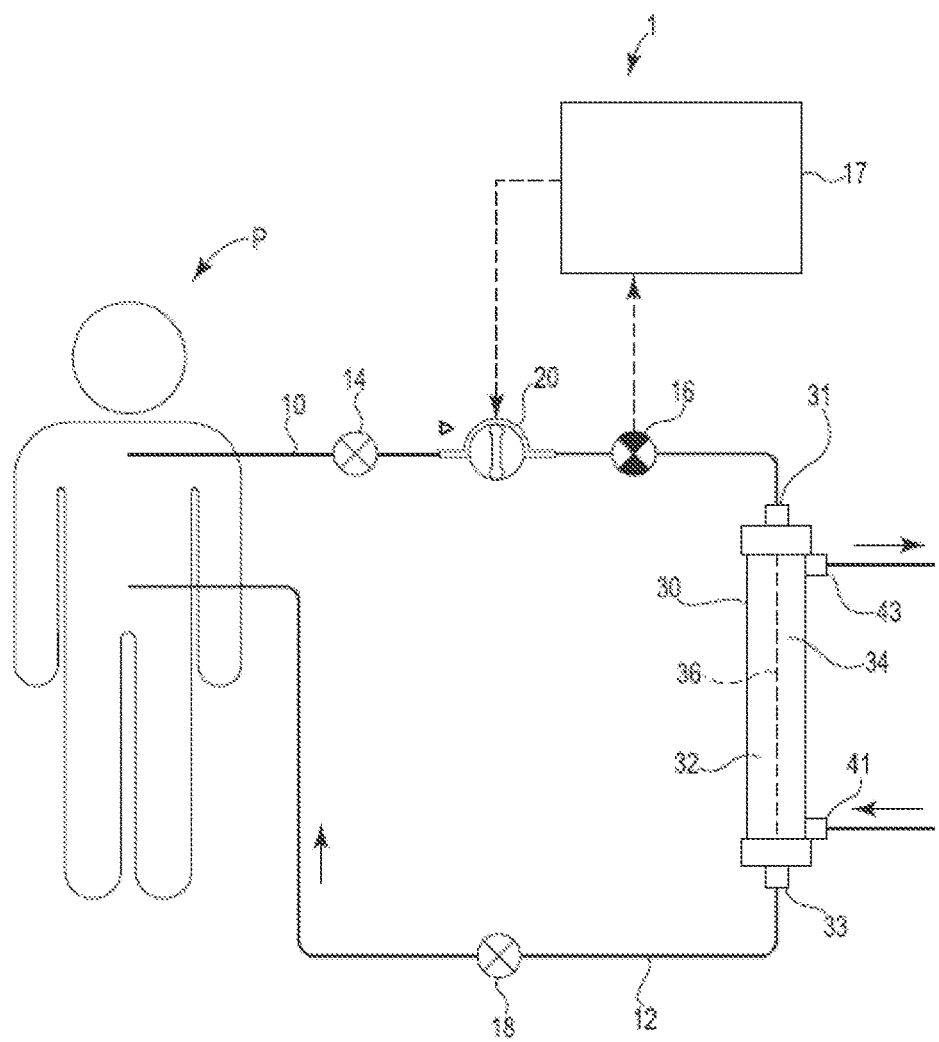
FIG. 1 depicts a schematic diagram of an illustrative embodiment of an extracorporeal blood treatment apparatus described herein.

In the following detailed description, reference is made to the accompanying drawings that form a part hereof, and in which are shown by way of illustration several specific embodiments. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above those other elements.

As used herein, when an element, component or layer for example is described as forming a "coincident interface" with, or being "on" "connected to," "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as being "directly on," "directly connected to," "directly coupled with," or "directly in contact with" another element, there are no intervening elements, components or layers for example.

As used herein, "have", "having", "include", "including", "comprise", "comprising" or the like are used in their open ended sense, and generally mean "including, but not limited to." It will be understood that the terms "consisting of" and "consisting essentially of" are subsumed in the term "comprising," and the like.

The term "pressure" or "pressure value" refers to both an absolute pressure value and to a pressure value gradient, pressure value transient or pressure variation.

This disclosure relates to extracorporeal blood treatment apparatus and methods and particularly to non-invasive pressure sensing of a blood circuit, among other aspects. The extracorporeal blood treatment apparatus includes a non-invasive pressure sensor disposed about an exterior surface of a blood line and coupled to a controller that is configured to operate control elements on the blood line or blood circuit. During a high pressure or occlusion event in the blood line, the sensor can provide a high pressure signal to the controller and the controller can act on the extracorporeal blood treatment apparatus to minimize clotting or other damage quickly. Since the non-invasive pressure sensor does not come into contact with any fluids, it can be reused continuously. The non-invasive pressure sensor can also operate as a proximity sensor to ensure that the blood line is secured and in place prior to operating the extracorporeal blood treatment apparatus. While the present disclosure is not so limited, an appreciation of various aspects of the disclosure will be gained through a discussion of the examples provided below.

In the illustrative embodiment depicted in FIG. 1, an extracorporeal blood treatment apparatus 1 includes a blood circuit having an arterial line 10 that delivers blood from a patient P to a blood compartment 32 of a primary filter 30. The blood in the blood circuit is returned to the patient P through a venous return line 12. The blood compartment 32 of the primary filter 30 is separated from an dialysate compartment 34 in the primary filter 30 by a semipermeable membrane 36. Although the primary filter 30 is depicted simplistically as having only one blood compartment 32 and one dialysate compartment 34, the primary filter 30 depicted in FIG. 1 should not be construed to limit the apparatus and methods described herein to such a simple embodiment. For example, the blood compartments or the dialysate compartments in the primary filters of extracorporeal blood treatment apparatus described herein may be, e.g., defined by a plurality of hollow fibers constructed of a semipermeable material as is known in the art. For example the primary filter may be an hemofilter, a dialyzer, an ultrafilter or an hemodiafilter.

As the patient's blood moves through the blood compartment 32 along the membrane 36, undesirable matter or molecules (apheresis, plasmapheresis for example) in the blood are transported through the membrane 36 and into the dialysate in the dialysate compartment 34 (such that the dialysate is "loaded" with the undesirable matter or molecules from the blood).

The blood circuit of the apparatus 1 of FIG. 1 also includes a blood pump 20 that is configured to move blood through the blood compartment 32 of the primary filter 30, with the blood entering the blood compartment 32 through an inlet 31 to which the arterial line 10 is connected. Blood in the blood circuit leaves the blood compartment 32 through an outlet 33 to which the venous line 12 is connected. Although depicted as a roller pump, the blood pump 20 may be of any suitable design (e.g., a roller pump, piston pump, diaphragm pump, etc.) or other flow control mechanism (e.g., valves, clamps, etc.), etc.

The blood circuit depicted in FIG. 1 also includes one or more pressure sensors configured to measure pressure at various locations in the blood circuit. In the depicted embodiment, the blood circuit includes an access pressure sensor 14 located between the patient P and the blood pump 20. The access pressure sensor 14 may be used to monitor pressure in the arterial line 10 downstream of the patient P and upstream of the blood pump 20.

The blood circuit of FIG. 1 includes a non-invasive pre-filter pressure sensor 16 located downstream from the blood pump 20 and upstream of the blood chamber 32 of the primary filter 30. The non-invasive pre-filter pressure sensor 16 is used to monitor pressure in the arterial line 10 and pressure inside the blood compartment 32 of the primary filter 30.

A third pressure sensor in the form of a return pressure sensor 18 can be located along the venous return line 12 downstream of the blood compartment 32 of the primary filter 30 and upstream of the patient P. The return pressure sensor 18 monitors pressure in the blood circuit after the blood has passed through the blood compartment 32 and before it is returned to the patient P.

While the pre-filter pressure sensor 16 is illustrated as being a "non-invasive" pressure sensor, any one or more of the pressure sensors disposed along the blood circuit can be independently "non-invasive". The term "non-invasive pressure sensor" refers to a pressure sensor that does not contact the fluid or liquid being sensed for pressure. The non-invasive pre-filter pressure sensors described herein sense a force (or pressure) acting on an interior surface of the blood tubing and transmits through an exterior wall of the blood tubing and onto a load cell or sensor of the non-invasive pre-filter pressure sensor. The non-invasive pressure sensor can detect the pressure or change in pressure across a wall of a tubing such as a blood tubing. The non-invasive pressure sensor is in direct contact with the exterior surface of the blood line or blood tubing. The blood tubing can be removed from the non-invasive pre-filter pressure sensor and reinserted into the non-invasive pre-filter pressure sensor without interrupting the pressure or flow of liquid or blood through the blood tubing.

The non-invasive pressure sensor described herein can operate via number of different principals. In one or more embodiments the non-invasive pressure sensor can sense the absolute pressure within the blood circuit or blood line tubing. In one or more embodiments the non-invasive pressure sensor can sense the rate of pressure change within the blood circuit or blood line tubing.

Examples of non-invasive pressure sensor include piezoresistive sensors, bending beam sensors (foil type or silicon strain gauges, optical, capacitive and magnetic (Hall effect) sensors), or force sensing sensors (membrane switch which changes resistance inversely with applied force) or ultrasonic sensor. One exemplary non-invasive ultrasonic pressure sensor is commercially available under the trade designation PRO Occlusion Detector from Introtek International, Edgewood, N.Y. The PRO Occlusion Detector employs pulse-type ultrasound and this sensor detects changes in pressure through the tubing wall and produces a corresponding passive resistive output signal. Another exemplary non-invasive pressure sensor is a ceramic piezoresistive pressure sensor commercially available under the trade designation Tube Contact Type from Morgan Technical Ceramics ElectroCeramics, Southampton, UK. Another exemplary non-invasive pressure sensor is a resister bridge pressure sensor commercially available under the trade designation Medical Pump Occlusion Sensor from SMD Sensors, Wallingford, Conn.

The extracorporeal blood treatment apparatus 1 depicted in FIG. 1 also includes a dialysate circuit configured to move dialysate through the dialysate compartment 34 of the primary filter 30. In the dialysate circuit, the dialysate enters the dialysate loading compartment 34 of the primary filter through an inlet 41 and leaves the dialysate compartment 34 through an outlet 43.

A control unit 17 is operably connected to the non-invasive pressure sensor 16 and control elements of the blood circuit. The control elements may include the blood pump 20. The control unit 17 is configured to monitor a blood circuit pressure value using the non-invasive pressure sensor 16 and operate the control elements (the blood pump 20, for example) of the blood circuit based on the monitored blood circuit pressure value.

Various components of the extracorporeal blood treatment apparatus described herein that may be operably connected to the control unit 17. The non-invasive pressure sensor 16 and the blood pump 20 of the blood circuit are operably connected to the control unit 17. In addition, other control elements of the blood circuit can also operably connected to the control unit 17. These other control elements include flow control devices such as valves, clamps and pumps for example, and pressure sensors such as the return pressure sensor 18 and access pressure sensor 14 for example.

The control unit 17 may be provided in any suitable form and may, for example, include memory and a controller. The controller may, for example, be in the form of one or more microprocessors, Application Specific Integrated Circuit (ASIC) state machines, etc. The control unit 17 may include one or more of any suitable input devices configured to allow a user to operate the apparatus (e.g., keyboards, touchscreens, mice, trackballs, etc.), as well as display devices or user interfaces configured to convey information to a user (e.g., monitors (which may or may not be touchscreens), indicator lights, etc.).

In one or more embodiments the control unit 17 is configured to take action once the blood circuit or blood line pressure value is not within a predetermined value range. This action can include at least one of, providing an alarm indication, or altering a flow rate of the blood pump 20. The selected or predetermined value range for the blood line pressure may be a single selected value (that is, the range may be a single set point), while in one or more other embodiments, the selected value range for the circuit pressure may include an upper limit and a lower limit that are two different values. In one or more embodiments, an example of a possible upper limit may be, e.g., 500 mmHg (absolute value) or 200 mmHg/sec (gradient). In one or more embodiments, an example of a possible lower limit may be, e.g., 300 mmHg (absolute value) or 100 mmHg/sec (gradient). The actual values for the upper and lower pressure limits (as either absolute or gradient) may, in one or more embodiments, depend on other factors such as, e.g., blood return pressure in the blood circuit, etc.

During a high pressure event in the blood line or blood circuit (for example pressure exceeding 500 mmHg absolute pressure or 200 mmHg/sec pressure gradient), the non-invasive pressure sensor 16 can provide a high pressure signal to the controller 17 and the controller can act on the control elements of the blood circuit such as reducing or ceasing the blood pump flow 20 and providing an alarm indication to a user interface, for example.

Figure 2:
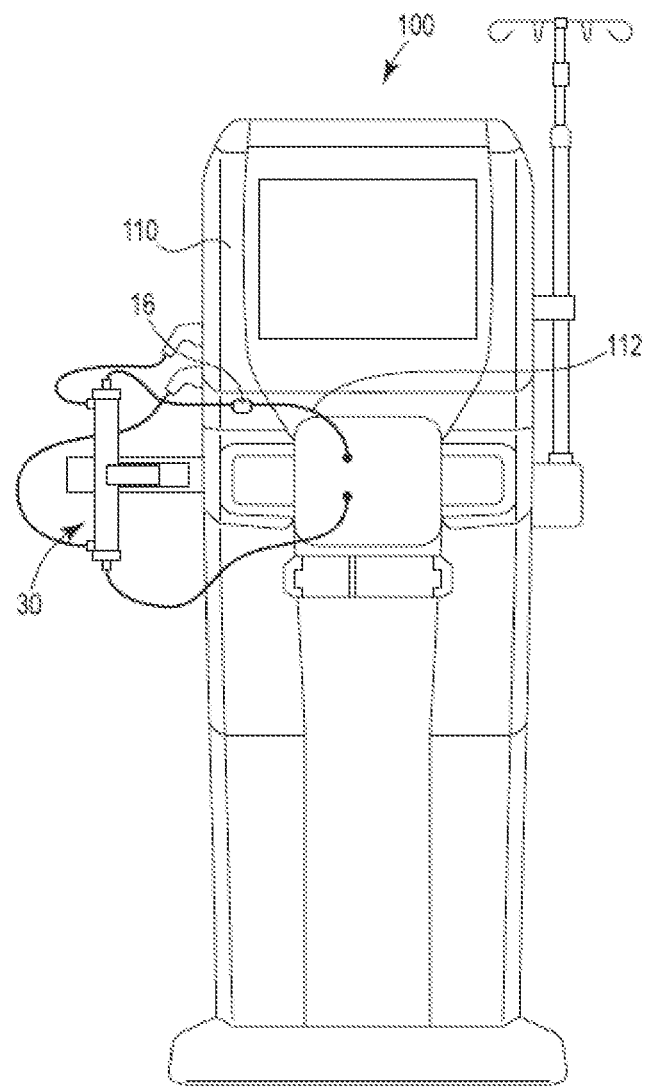
FIG. 2 depicts an illustrative dialysis therapy unit.
Figure 3:
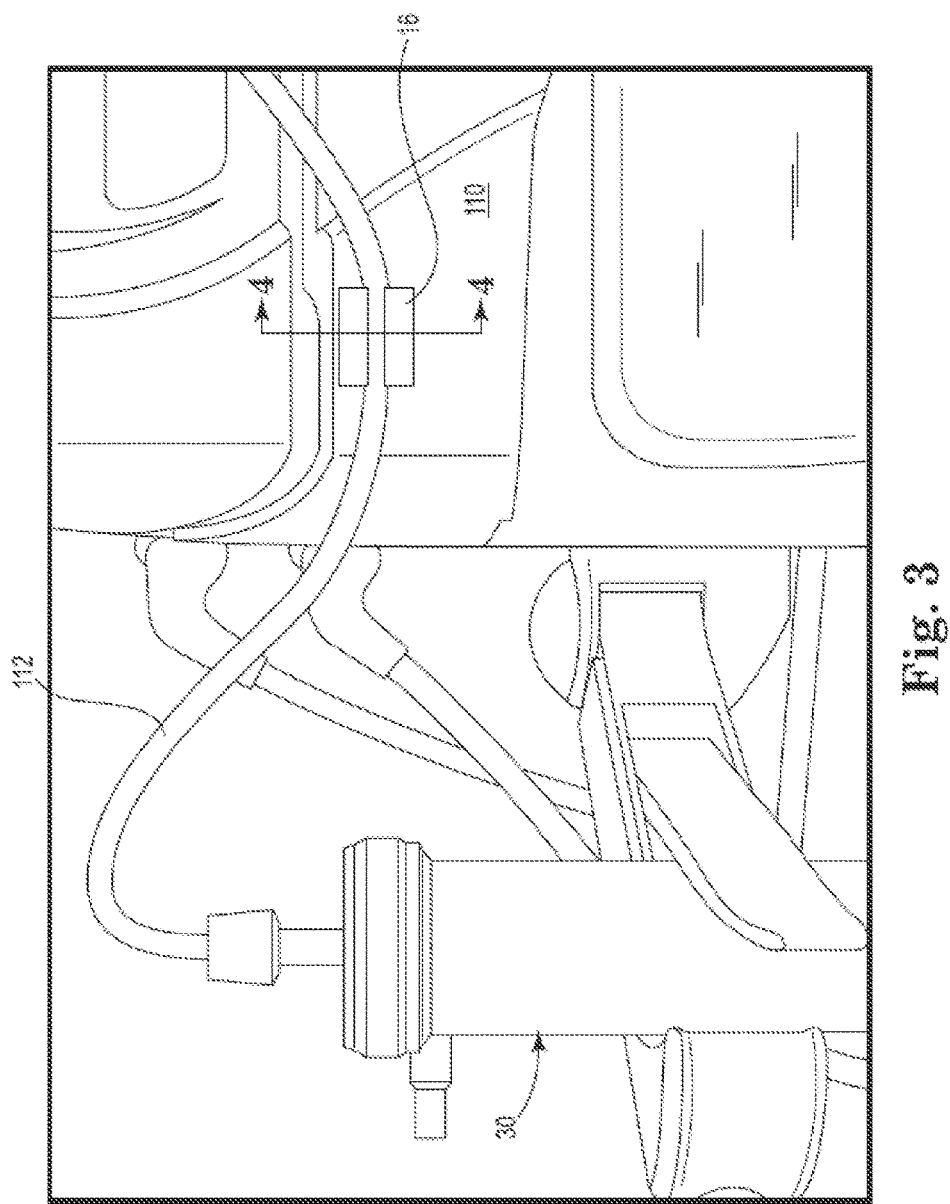
FIG. 3 depicts an close-up view of an illustrative placement of a non-invasive pressure sensor on the dialysis therapy unit shown in FIG. 2.
Figure 4:
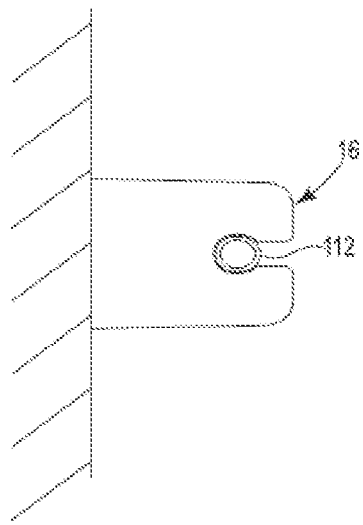
FIG. 4 depicts a cross-sectional view of an illustrative non-invasive pressure sensor engaged with a blood circuit taken along line 4-4 of FIG. 3.
Figure 5:
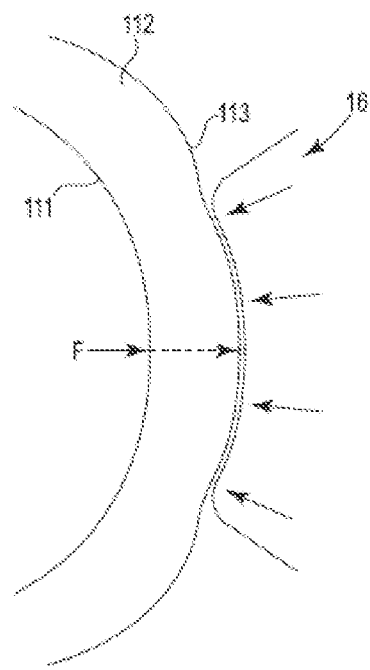
FIG. 5 depicts a close-up schematic view of the non-invasive pressure sensor engaged with a blood circuit in FIG. 4.

FIG. 2 depicts an illustrative dialysis therapy unit 100. FIG. 3 depicts an close-up view of an illustrative placement of a non-invasive pressure sensor 16 on the dialysis therapy unit 100 shown in FIG. 2. FIG. 4 depicts a cross-sectional view of an illustrative non-invasive pressure sensor 16 engaged with a blood circuit 112 taken along line 4-4 of FIG. 3. FIG. 5 depicts a close-up schematic view of the non-invasive pressure sensor engaged 16 with a blood circuit 112 in FIG. 4.

In one or more embodiments, the non-invasive pressure sensor 16 is fixed to a housing 112 of the apparatus 100 and the blood line 112 is removable from the non-invasive pressure sensor 16. The non-invasive pressure sensor 16 can take any useful form other than the specific constructions illustrated in these Figures. FIG. 2 illustrates the non-invasive pressure sensor 16 on or fixed to a front panel or on or fixed to a front surface 112 of the extracorporeal blood treatment apparatus 100. The non-invasive pressure sensor 16 can be on or fixed to any surface of the extracorporeal blood treatment apparatus 100 housing that is convenient to engage and disengage the blood line 112 from the non-invasive pressure sensor 16.

In one or more embodiments, the blood line 112 is formed of polymeric tubing that is deformable and can apply a force that is a function of a pressure F found within the blood line 112 polymeric tubing. The non-invasive pressure sensor 16 is in direct contact with an exterior surface 113 of the polymeric tubing. The pressure within the blood line 112 applies a force F to an interior surface 111 of the blood line 112 polymeric tubing according to a pressure of the liquid within the blood line 112 polymeric tubing. This force F is transferred through the wall of the blood line 112 polymeric tubing and applies a load or force onto the non-invasive pressure sensor 16 at the exterior surface 113 of the polymeric tubing.

In one or more embodiments, the non-invasive pressure sensor 16 is in direct contact with opposing sides of the blood line 112 polymeric tubing. The non-invasive pressure sensor 16 is configured to sense a force F applied by the blood to the blood line 112 polymeric tubing.

In one or more embodiments, the non-invasive pressure sensor 16 does not have a fine accuracy. Since the non-invasive pressure sensor 16 is providing a gross high pressure alarm in many embodiments, the non-invasive pressure sensor 16 can have a lower accuracy and can sense large pressure transients. In many embodiments, the non-invasive pressure sensor 16 has an accuracy that is not less than ±50 mmHg, or is not less than ±25 mmHg, or is not less than ±15 mmHg.

In one or more embodiments of a method of moving blood through a blood circuit in an extracorporeal blood treatment apparatus the method includes: pumping blood through the blood circuit at a blood flow rate with the blood pump 20; measuring blood circuit pressure with the non-invasive pressure sensor 16; and altering control elements of the blood circuit based on the measured blood circuit pressure, as described above. In many embodiments, the altering step can include altering a flow rate of the blood pump 20 when the measured blood circuit pressure is greater than a predetermined value.

In one or more embodiments, the altering step includes providing an alarm indication to a user interface or deactivating the blood pump 20 when the measured blood circuit pressure indicates that the blood circuit is not engaged within the non-invasive pressure sensor 16 or when the measured blood circuit pressure is greater than a predetermined value. Thus, the non-invasive pressure sensor 16 can operate as a proximity sensor to ensure that the blood line 112 is secured and in place prior to operating the extracorporeal blood treatment apparatus 100.

In one or more embodiments, the method further includes removing the blood line 112 from the non-invasive pressure sensor 16 upon completion of a treatment. Since fluid from the blood line 112 does not contact portion of the non-invasive pressure sensor 16 and the non-invasive pressure sensor 16 remains fixed to the housing 110 of the extracorporeal blood treatment apparatus 100 the blood line 112 can be removed and either separately cleaned or simply replaced with a sterile blood line 112 and reengaged with the non-invasive pressure sensor 16.

The complete disclosure of the patents, patent documents, and publications identified herein are incorporated by reference in their entirety as if each were individually incorporated.

Thus, embodiments of EXTRACORPOREAL BLOOD CIRCUIT WITH NON-INVASIVE PRESSURE SENSOR are disclosed. One skilled in the art will appreciate that the compositions described herein can be practiced with embodiments other than those disclosed. The disclosed embodiments are presented for purposes of illustration and not limitation. Accordingly, the invention is to be limited only by the claims provided below and equivalents thereof.

The invention claimed is:

1. An apparatus configured to remove one or more substances from blood, wherein the apparatus comprises:
a primary filter comprising a first semipermeable membrane separating a blood compartment from a dialysate loading compartment;
a blood circuit having a blood line connected to the blood compartment of the primary filter;
a non-invasive pressure sensor configured to directly contact any exposed longitudinal portion of an exterior surface of a circular tube forming the blood line, the non-invasive pressure sensor further configured to sense pressure in the blood line, wherein the non-invasive pressure sensor includes an outer wall forming a groove leading to a sensing portion in direct contact with the exterior surface of the blood line and does not contact liquid in the blood line, the groove narrower than the sensing portion to compress the blood line upon insertion through the groove such that the blood line when uncompressed is held within the sensing portion after the insertion; and
a control unit operably connected to the non-invasive pressure sensor and to control elements of the blood circuit, wherein the control unit is configured to:
monitor a blood circuit pressure value using the non-invasive pressure sensor and operate the control elements of the blood circuit based on the monitored blood circuit pressure value, wherein operating the control elements comprises deactivating the blood pump when the monitored blood circuit pressure indicates that the blood line is not engaged with the non-invasive pressure sensor.

2. An apparatus according to claim 1, wherein the non-invasive pressure sensor is in direct contact with the exterior surface of the blood line.

3. An apparatus according to claim 1, wherein the blood line comprises polymeric tubing, and the non-invasive pressure sensor is in direct contact with an exterior surface of the polymeric tubing.

4. An apparatus according to claim 3, wherein the non-invasive pressure sensor is in direct contact with opposing sides of the polymeric tubing.

5. An apparatus according to claim 3, wherein the non-invasive pressure sensor is configured to sense a force applied by the blood to the polymeric tubing.

6. An apparatus according to claim 1, wherein the non-invasive pressure sensor is fixed to an external surface of a housing of the apparatus, and wherein the groove being narrower than the sensing portion to compress the blood line enables the blood line to be removed through the groove from the non-invasive pressure sensor and reinserted through the groove into the non-invasive pressure sensor while continuing to allow flow of liquid through the blood line.

7. An apparatus according to claim 1, wherein the control unit is configured to take action once a blood circuit pressure absolute value or blood circuit pressure gradient is not within a predetermined value range.

8. An apparatus according to claim 7, wherein the control unit action includes providing an alarm indication.

9. An apparatus according to claim 1, wherein the control elements comprise a blood pump configured for causing a fluid flow rate through the blood line.

10. An apparatus according to claim 9, wherein the blood circuit has an arterial line that is configured to deliver blood from a patient to said blood compartment of the primary filter, and a venous line that is configured to return treated blood to the patient, wherein said blood pump is positioned in correspondence of and active on said arterial line.

11. An apparatus according to claim 10, wherein the non-invasive pressure sensor is located downstream from the blood pump and upstream of the blood chamber of the primary filter.

12. An apparatus according to claim 11, wherein the blood circuit includes an access pressure sensor of a type different than the non-invasive pressure sensor, the access pressure sensor located between an end of the arterial line connectable to the patient and the blood pump.

13. An apparatus according to claim 7, wherein the control unit action includes altering a flow rate of the blood pump.

14. An apparatus according to claim 1, wherein the non-invasive pressure sensor has an accuracy that is not less than ±25 mmHg.

15. An apparatus according to claim 1, wherein the non-invasive pressure sensor comprises a sensing portion in direct contact with the exterior surface of the blood line and does not contact liquid in the blood line.

16. An apparatus according to claim 7, wherein the control unit action includes reducing a flow rate caused by the blood pump by reducing the blood pump angular speed when at least one of pressure absolute value and pressure gradient falls outside a respective acceptable pressure range.

17. The apparatus according to claim 1, wherein the non-invasive pressure sensor includes a circular seat configured to directly contact the exposed longitudinal portion of the exterior surface of the circular tube forming the blood line.

18. An apparatus configured to remove one or more substances from blood, wherein the apparatus comprises:
a primary filter comprising a first semipermeable membrane separating a blood compartment from a dialysate loading compartment;
a blood circuit having a blood line connected to the blood compartment of the primary filter;
a non-invasive pressure sensor disposed about an exterior surface of the blood line, the non-invasive pressure sensor being configured to sense pressure in the blood line, wherein the non-invasive pressure sensor comprises an outer wall forming a groove leading to a sensing portion in direct contact with the exterior surface of the blood line and does not contact liquid in the blood line, the groove narrower than the sensing portion to compress the blood line upon insertion through the groove such that the blood line when uncompressed is held within the sensing portion after the insertion, and such that the blood line may be removed through the groove from the non-invasive pressure sensor and reinserted through the groove into the non-invasive pressure sensor while continuing to allow flow of liquid through the blood line; and a control unit operably connected to the non-invasive pressure sensor and to control elements of the blood circuit, wherein the control unit is configured to:
  monitor a blood circuit pressure value using the non-invasive pressure sensor,
  take action when at least one of a blood circuit pressure absolute value and blood circuit pressure gradient is not within a predetermined value range, wherein the control unit action comprises one or both of providing an alarm indication and altering a flow rate of the blood pump when the monitored blood circuit pressure indicates that the blood line is not engaged with the non-invasive pressure sensor.

19. An apparatus according to claim 18, wherein the blood line comprises polymeric tubing, and the non-invasive pressure sensor is in direct contact with an exterior surface of the polymeric tubing, wherein the non-invasive pressure sensor is configured to sense a force applied to the polymeric tubing by liquid in the polymeric tubing, and wherein the non-invasive pressure sensor is fixed to a housing of the apparatus.

20. An apparatus configured to remove one or more substances from blood, wherein the apparatus comprises:
  a primary filter comprising a first semipermeable membrane separating a blood compartment from a dialysate loading compartment;
  a blood circuit having a blood line connected to the blood compartment of the primary filter;
  a non-invasive pressure sensor disposed about an exterior surface of the blood line, the non-invasive pressure sensor being configured to sense pressure in the blood line, wherein the non-invasive pressure sensor comprises an outer wall forming a groove leading to a sensing portion that is placed in direct contact with the exterior surface of the blood line and does not contact liquid in the blood line, the groove narrower than the sensing portion to compress the blood line upon insertion through the groove such that the blood line when uncompressed is held within the sensing portion after the insertion, and such that the blood line may be removed through the groove from the non-invasive pressure sensor and reinserted through the groove into the non-invasive pressure sensor while continuing to allow flow of liquid through the blood line; and
  a control unit operably connected to the non-invasive pressure sensor and to control elements of the blood circuit, wherein the control unit is configured to:
    monitor a blood circuit pressure value using the non-invasive pressure sensor,
    take action when at least one of a blood circuit pressure absolute value and blood circuit pressure gradient is not within a predetermined value range, wherein the control unit action includes deactivating the blood pump when the monitored blood circuit pressure indicates that the blood line is not engaged with the non-invasive pressure sensor.

21. An apparatus according to claim 20, wherein the blood line comprises polymeric tubing, and the non-invasive pressure sensor is in direct contact with an exterior surface of the polymeric tubing, wherein the non-invasive pressure sensor is configured to sense a force applied to the polymeric tubing by liquid in the polymeric tubing, and wherein the non-invasive pressure sensor is fixed to an external surface of a housing of the apparatus.

* * * * *